(12) United States Patent
Allen

(10) Patent No.: US 8,061,372 B1
(45) Date of Patent: Nov. 22, 2011

(54) ORTHODONTIC FLOSSING IMPLEMENT

(76) Inventor: Margarita B. Allen, Safety Harbor, FL (US)

(*) Notice: Subject to any disclaimer, the term of this patent is extended or adjusted under 35 U.S.C. 154(b) by 515 days.

(21) Appl. No.: 12/231,440

(22) Filed: Sep. 3, 2008

(51) Int. Cl.
*A61C 15/00* (2006.01)
(52) U.S. Cl. .................................... 132/329; 132/323
(58) Field of Classification Search ............ 132/321, 132/329, 323; D28/66
See application file for complete search history.

(56) References Cited

U.S. PATENT DOCUMENTS

| | | | |
|---|---|---|---|
| 4,133,339 A | 1/1979 | Naslund |
| D265,515 S | 7/1982 | Levine |
| 5,050,625 A | 9/1991 | Siekmann |
| 5,183,063 A | 2/1993 | Ringle et al. |
| 5,184,631 A | 2/1993 | Ikeda |
| 5,289,836 A | 3/1994 | Peng |
| 5,482,466 A | 1/1996 | Haynes |
| 5,638,841 A | 6/1997 | Levine |
| 5,735,299 A | 4/1998 | Kaltenbach |
| 5,899,214 A | 5/1999 | Francis |
| 6,488,036 B1 | 12/2002 | Francis |
| 6,814,086 B2 | 11/2004 | Stallings |

FOREIGN PATENT DOCUMENTS

GB 2122495 * 1/1984

* cited by examiner

*Primary Examiner* — Rachel Steitz
(74) *Attorney, Agent, or Firm* — Charles J. Prescott

(57) ABSTRACT

An orthodontic flossing implement for facilitating positioning and manipulating of a portion of a length of dental floss into the interdental space between adjacent teeth and proximate to and beneath an orthodontic wire which defines an arch extending between adjacent orthodontic brackets on the teeth. An elongated handle dependently supports an elongated, slender shaft formed as a unit with, and extending from a proximal end of the handle. The shaft is dimensionally smaller in thickness than that of said handle and preferably oriented at an acute angle to the handle. A tip, formed as a unit with, and extending from a second end of the shaft, is oriented at an acute angle to the handle, the tip having an aperture formed therethrough sized to just receive a length of dental floss. The tip with the dental floss positioned through said aperture, is manipulable by said handle to pass beneath an arch of the orthodontic wire and to floss the interdental tissue.

4 Claims, 3 Drawing Sheets

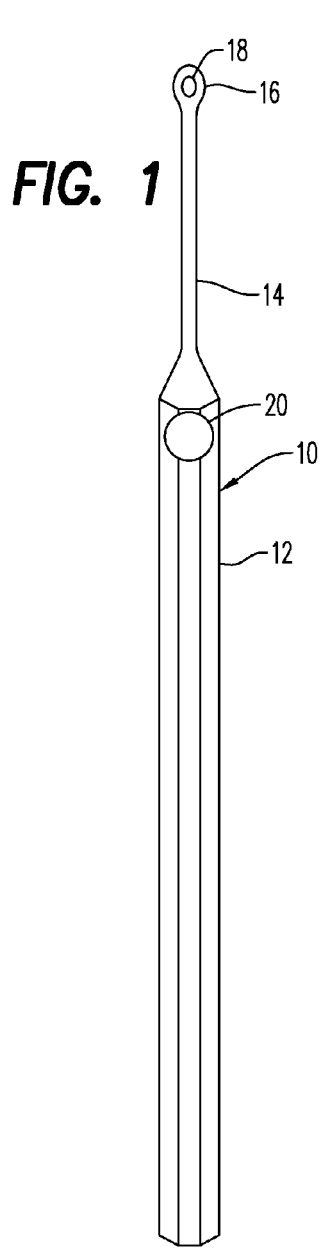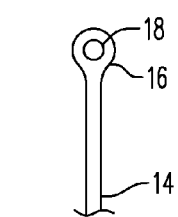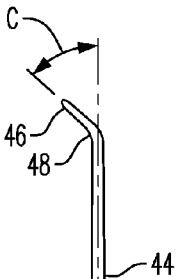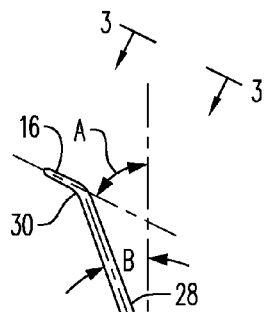

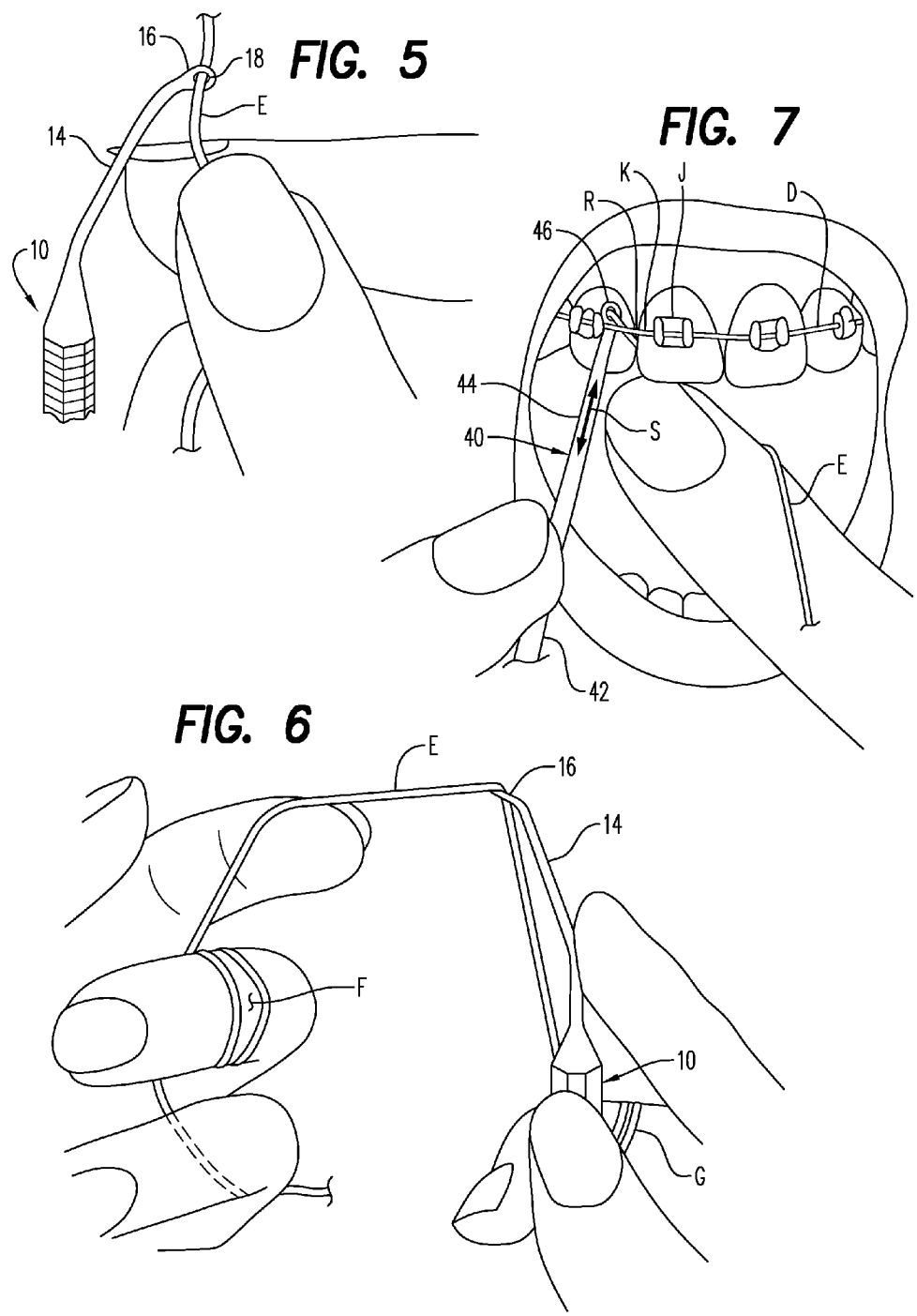

ORTHODONTIC FLOSSING IMPLEMENT

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to dental hygiene devices, and more specifically to an orthodontic flossing implement and method of use thereof, wherein the present invention facilitates thorough inter-dental flossing of orthodontically-treated teeth and, in particular, teeth fitted with braces.

2. Description of Related Art

In a majority of the cases, persons requiring orthodontic treatment including orthodontic appliances in the form of fixed braces are children, pre-teens and teenagers. Prior art devices require a great amount of time, dexterity, and effort to reach the posterior clearances of the upper and lower arches. These flossing devices are either too small to comfortably hold and/or too small to access the posterior molar clearances or too big to fit between the inter-proximal space of adjacent teeth and/or to fit under the arch wire of the appliance at the clearance. Prior art devices also are not strong enough to easily cut through the tight contacts of adjacent teeth or to properly remove the bacterial plaque from the interproximal surface of the teeth and gums at the arch (clearance).

With some prior art devices, patient compliance to daily flossing is near impossible, rendering the patient susceptible to bacterial plaque damaging effects to the gums, teeth and the surrounding jawbones.

U.S. Pat. No. 5,050,625 to Siekmann teaches a dental floss threading device which permits insertion of dental floss between dental structures and aids in cleaning areas abutting dental structures such as orthodontic devices. A device and method for flossing and including an eyelet (FIG. 5) is disclosed in U.S. Pat. No. 5,638,841 to Levine.

Francis teaches dental flossing devices in U.S. Pat. Nos. 5,899,214 and 6,488,036 which provide a flexible flosser with unrestricted maneuverability within the clearance, providing easier insertion and increased cleaning efficiency. Haynes discloses a similar instrument in U.S. Pat. No. 5,482,466 which facilitates flossing and is utilizable by persons fitted with orthodontic braces.

An integrally formed dental floss and leader that lends itself to oral prophylaxis especially for implants and bridges is disclosed in U.S. Pat. No. 5,183,063 to Ringle, et al. and dental floss with a guide post is taught by Peng in U.S. Pat. No. 5,289,836. Similarly, Stallings discloses an orthodontic flossing device for removing debris from in between the proximal surfaces of teeth undergoing orthodontic treatment in U.S. Pat. No. 6,814,086.

A needle for leading dental floss through narrow apertures is disclosed in U.S. Pat. No. 4,133,339 to Nashlund. This plastic needle-like design with an opening for the floss is very inconvenient and time consuming to use. Accessibility of posterior clearances is difficult and the small floss threader has to be threaded through each and all possible (arch sites) clearances. Ikeda discloses a device for cleaning teeth of orthodontic patients in U.S. Pat. No. 5,184,631 and, when in use, inserting the device at the clearance, a small hook member on the facial prong is used as leverage to proceed with cleaning. This hook member catches on the arch wire and makes this device tedious to use.

Kaltenbach teaches a device useful for inserting dental floss between teeth and under dental bridges in U.S. Pat. No. 5,735,299 and a design patent to Levine, D265,515, shows a dental flossing instrument.

U.S. Pat. No. 5,890,500 to Mabon, et al. teaches a device and process for flossing comprising a length of thin guide tubing combined with the application of conventional dental floss. Striebel teaches dental floss for brace wearers and the like including a semi-rigid threader and curvature formed substantially along its whole length in U.S. Pat. No. 5,392,794.

A flossing tool having a floss spool cavity and handle is disclosed in U.S. Pat. No. 5,482,466 to Haynes in which the primary object is to direct floss into interproximal spaces which are bounded by an arch wire where the tool angle makes it difficult if not near impossible to access posterior arches and/or clearances.

The foregoing examples of the related art and limitations related therewith are intended to be illustrative and not exclusive. Other limitations of the related art will become apparent to those skilled in the art upon a reading of the specification and a study of the drawings.

The present invention teaches a uniquely configured orthodontic flossing element which has more favorable use structure for easily and effectively not only positioning a length of dental floss between the wire arch and the facial surfaces of adjacent teeth, but also facilitates the manual manipulation of either the implement and/or the free end of the dental floss through the contact of adjacent teeth to effectively, quickly, easily and properly clean the interdental spaces and tissues between adjacent teeth at all anterior and posterior clearance sites of the upper and lower jaws.

BRIEF SUMMARY OF THE INVENTION

This invention is directed to an orthodontic flossing implement for facilitating positioning and manipulating of a portion of a length of dental floss through the contact and into the interdental space between adjacent teeth and proximate to an orthodontic wire which defines an arch (clearance) extending between adjacent orthodontic brackets on the teeth. An elongated handle dependently supports an elongated, slender shaft formed as a unit with, and extending from a proximal end of the handle. The shaft is dimensionally smaller in thickness than that of said handle and preferably oriented at an acute angle to the handle. A tip, formed as a unit with, and extending from a second end of the shaft, is oriented at an acute angle to the handle, the tip having an aperture formed therethrough sized to just receive a length of dental floss. The tip with the dental floss positioned through said aperture, is manipulable by said handle to pass beneath an arch of the orthodontic wire and to floss the interdental tissues at all 26 possible arches (clearances) continuously and quickly with ease, thus encouraging patient daily flossing compliance as prescribed by their dental professional.

It is therefore an object of this invention to provide an improved orthodontic flossing implement for maintaining healthy interdental tissues between adjacent teeth of a person wearing orthodontic braces.

Still another object of this invention is to provide an orthodontic flossing implement having improved structural features which greatly facilitate the maintaining of healthy interdental tissue of an orthodontic brace-wearing patient.

Yet another object of this invention is to provide an orthodontic flossing implement which will enable patients undergoing permanent orthodontic treatment easy and quick daily flossing routines for all twenty-six (26) possible intradental space tissue sites.

And another object of this invention is to provide an orthodontic flossing implement which will enable patients whose oral anatomy makes it difficult to access the posterior and retromolar areas comfortably and with ease.

Still another object of this invention is to provide an orthodontic flossing implement for holding and guiding dental floss and fitting into the narrow, tight confines of the clearance between the facial interproximal/interdental contacts of adjacent teeth and the arch wire and between the orthodontic brackets permanently cemented to the teeth.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

FIG. 1 is a front elevation view of the preferred embodiment of the invention.

FIG. 2 is a side elevation view of FIG. 1.

FIG. 3 is a view in the direction of arrows 3-3 in FIG. 2.

FIG. 4 is a side elevation view of an alternate embodiment of the invention.

FIG. 5 is a perspective view showing threading of a length of dental floss through the tip of the implement shown in FIGS. 1 and 2.

FIG. 6 is another perspective view showing the implement with dental floss threaded therethrough ready for positioning and use.

FIG. 7 is a view of the implement shown in FIG. 4 in use flossing the interdental tissue between two adjacent teeth beneath a wire arch.

Figure 8:
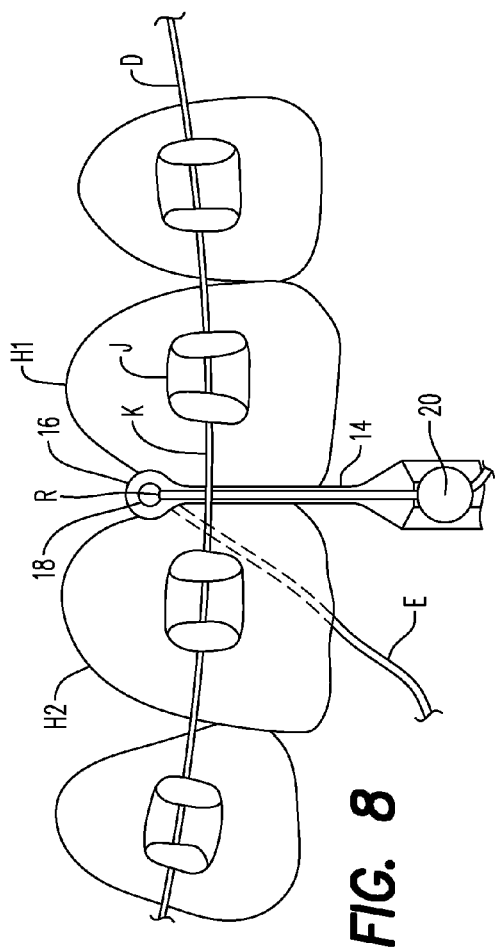
FIG. 8 is a front elevation view of the embodiment of FIGS. 1 and 2 in use.

Exemplary embodiments are illustrated in reference figures of the drawings. It is intended that the embodiments and figures disclosed herein are to be considered to be illustrative rather than limiting.

DETAILED DESCRIPTION OF THE INVENTION

Referring now to the drawings, and firstly to FIGS. 1 to 3, the preferred embodiment of the invention is there shown generally at numeral 10. This orthodontic flossing implement 10 is preferably formed of surgical steel which may be autoclaved for repeated use in a professional practice by a dental practitioner on a patient and for personal oral hygiene at home. An elongated handle 12 preferably textured for secure grasping and better manipulation (not shown) is formed as an elongated octagonal shape dimensionally narrowing into a shaft 14 which, in front elevation, is substantially straight as shown in FIG. 1.

However, in FIG. 2, the shaft 14 includes a bend 26 between shaft portions 24 and 28 defining an acute angle B between the longitudinal axis of the handle 12 and the main portion of the shaft 14.

Disposed at the upper or distal end of the shaft 14 is a generally flat circular tip 16 which is oriented to the shaft about bend 30 so as to define another acute angle A with respect to the longitudinal axis of the handle 12. As best seen in FIG. 3, the tip 16 is generally circular and flattened in nature and includes an aperture 18 sized for convenient passage of a filament of dental floss therethrough as will be described herebelow. The entire flossing implement 10 is preferably formed as a unit for strength and sanitizing purposes.

The preferred range of acute angles with respect to angle B is typically in the range of about 20° to 40°. However, the more important angle orientation is with respect to the tip 16 vis-a-vis the longitudinal axis of handle 12. This acute angle A is preferably in the range of 30° to 80° or at least 20°. At 20° of angle A, the user cannot observe the lower shaft portion 14 and thus effectiveness is lost. At an angle A above 80°, the user cannot observe even the tip 16 as the user's hand will also be in the way of that observation. Moreover, at the angle of near orthogonal with respect to angle A, the vertical positioning of the tip 16 by handle movement it becomes problematic.

Referring now to FIG. 4, an alternate embodiment of the invention is there shown generally at numeral 40 and includes an elongated slender textured handle 42 which reduces substantially in dimensional sizing down to define elongated shaft 44 which is oriented coaxially with handle 42 in all views. Only the tip 46 is angularly oriented about bend 48 at an angle C. This acute angle C is again in the range of about 30° to 80° or at least greater than 20°.

As also seen in FIGS. 1 to 4, each embodiment 10 and 40 includes a floss anchor 20 which is connected to the proximal end of the handle 12 or 42 and having a disc or button shape and being spaced away from the side of the handle 12 or 42 a distance 22 as seen in FIG. 2. This gap 22 is sized to receive a number of turns of dental floss therearound to secure and stabilize the dental floss thereabout as will be described more fully herebelow.

Referring now to FIGS. 5 and 6, preparation for and use of the flossing implement 10 is there shown. As seen in FIG. 5, a length of dental floss E is manually passed through the aperture 18. Thereafter, the proximal end of the dental floss E is secured around the floss anchor 20 in a fashion best seen in FIGS. 8 and 9. Alternately, as seen in FIG. 6, the dental floss E may be manually secured at F and G around the corresponding fingers of the user for tensioning of the dental floss E in the vicinity of the tip 16 for proper use described herebelow.

Figure 9:
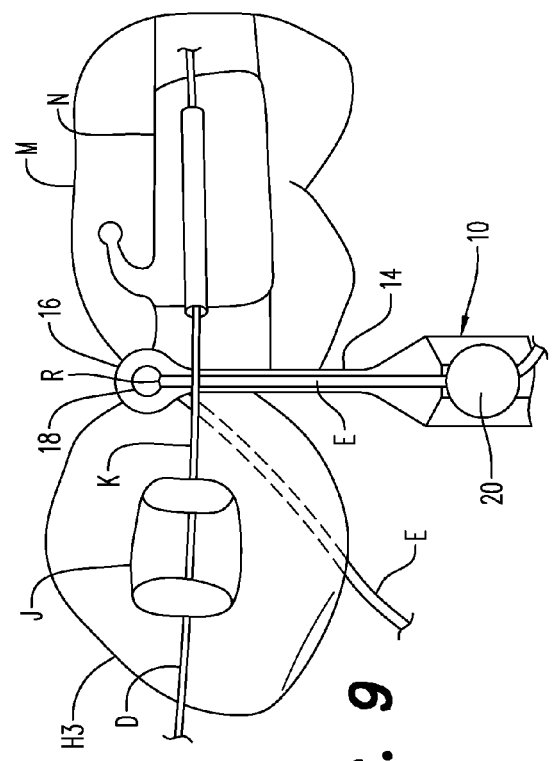
FIG. 9 is a side elevation view of the implement of FIGS. 1 and 2 in use cleaning the interdental tissue between adjacent posterior facial (buccal) teeth clearance.
Figure 10:
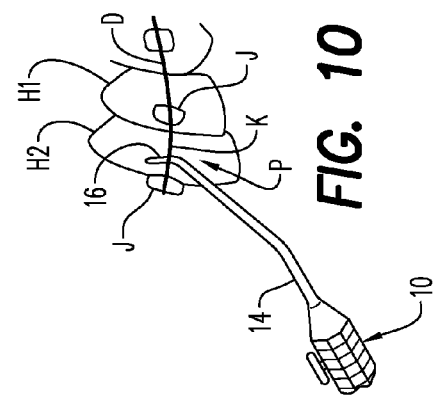
FIG. 10 is a side elevation view of FIG. 8.

As seen in FIGS. 8 to 10, the tip 16 (absent the dental floss for clarity in FIG. 10) is moved upwardly in the direction of arrow P beneath the arch K of the orthodontic wire D which passes between and is anchored and tightened against each of the orthodontic brackets J which have been cemented centrally on the facial surface to the proximal side of each of the teeth shown typically at H, H1, H2, H3 . . . .

The tip 16 is upwardly positioned beneath each of the arches K so that the dental floss E is positioned immediately against the interdental tissue shown at R. With one end of the dental floss secured around anchor post 20, the user may then manually tension the other end of the dental floss E as best seen in FIG. 7, after which the dental floss E may be moved up and down by movement of the flossing implement 40 (or 10) in the direction of the arrow S. By continued proper manipulation of the dental floss E between all the interdental tissues R, a proper cleaning and healthy maintenance of the teeth and gums while the orthodontic braces are worn is maintained.

As seen in FIG. 9, the same procedure is utilized for the posterior facial (buccal) teeth between molar M and the premolar tooth H3 with the interdental, tissue R being scrubbed and thoroughly cleaned and stimulated to maintain healthy tooth and gum tissues.

Referring to FIG. 7, while a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. An orthodontic flossing implement for facilitating positioning and manipulating a portion of a length of dental floss into the interdental space between adjacent teeth and proximate to an orthodontic wire which defines an arch extending between adjacent orthodontic brackets on the teeth, said implement comprising:
   an elongated, substantially straight handle;
   an elongated, slender shaft having a first end thereof connected to and formed as a unit with, and extending from a proximal end of said handle;
   said shaft being substantially smaller in thickness than that of said handle and having a first acute angle bend therein proximate said handle and a second acute angle bend proximate to a distal tip of said shaft;
   said distal tip having a closed aperture formed therethrough, said aperture being sized to just receive a length of dental floss passing therethrough and to pass beneath an arch of the orthodontic wire while carrying the dental floss therewith to floss the interdental space.

2. An orthodontic flossing implement as set forth in claim 1, wherein:
   said second acute angle is in a range of about 30° to 80°.

3. An orthodontic flossing implement as set forth in claim 1, wherein:
   said second acute angle is greater than 20°.

4. An orthodontic flossing implement as set forth in claim 1, further comprising:
   a floss anchor connected to, and projecting from, a proximal portion of said handle, said floss anchor configured for releasable winding attachment of the dental floss thereto wherein tension in the dental floss passing through said aperture may be maintained with manual pressure.

* * * * *